(12) United States Patent
Goyal

(10) Patent No.: US 11,449,765 B2
(45) Date of Patent: Sep. 20, 2022

(54) MASS ESTIMATION OF PREPARED FOOD PRODUCTS

(71) Applicant: International Business Machines Corporation, Armonk, NY (US)

(72) Inventor: Munish Goyal, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 1025 days.

(21) Appl. No.: 16/148,158

(22) Filed: Oct. 1, 2018

(65) Prior Publication Data

US 2020/0104724 A1 Apr. 2, 2020

(51) Int. Cl.
| | | |
|---|---|---|
| *G06N 5/02* | (2006.01) | |
| *G06Q 50/12* | (2012.01) | |
| *G01N 29/44* | (2006.01) | |
| *G01N 29/11* | (2006.01) | |
| *G06N 20/00* | (2019.01) | |
| *G01N 29/26* | (2006.01) | |
| *G01N 33/02* | (2006.01) | |

(52) U.S. Cl.
CPC .............. *G06N 5/02* (2013.01); *G01N 29/11* (2013.01); *G01N 29/4481* (2013.01); *G06N 20/00* (2019.01); *G06Q 50/12* (2013.01); *G01N 29/262* (2013.01); *G01N 33/02* (2013.01); *G01N 2291/02818* (2013.01); *G01N 2291/02854* (2013.01)

(58) Field of Classification Search
CPC .............. G01N 29/11; G01N 29/4481; G01N 2291/02818; G01N 2291/02854; G01N 29/262; G06N 20/00; G06N 3/08; G06N 5/025; G06N 5/046; G06N 7/005; G06N 7/023

See application file for complete search history.

(56) References Cited

U.S. PATENT DOCUMENTS

| | | | | |
|---|---|---|---|---|
| 4,868,357 | A * | 9/1989 | Serikawa ............. | H05B 6/6411 219/706 |
| 5,671,362 | A | 11/1997 | Cowe et al. | |
| 2008/0210702 | A1 | 11/2008 | Lochinger et al. | |
| 2019/0029277 | A1* | 1/2019 | Skrædderdal et al. ..................... | A22C 17/002 |
| 2020/0334628 | A1* | 10/2020 | Goldberg ............. | G06K 9/6267 |
| 2021/0335475 | A1* | 10/2021 | Jeong ..................... | G01G 19/44 |

\* cited by examiner

*Primary Examiner* — Helen C Kwok
(74) *Attorney, Agent, or Firm* — Yee & Associates, P.C.

(57) ABSTRACT

A method, apparatus, system, and computer program product for estimating a mass of a prepared food product. An ultrasonic beam is steered by a computer system at the prepared food product on a platform. An estimate of a mass of the prepared food product on the platform is determined by the computer system using response signals detected in response to scanning the prepared food product on the platform with the ultrasonic beam.

17 Claims, 6 Drawing Sheets

MASS ESTIMATION OF PREPARED FOOD PRODUCTS

BACKGROUND

1. Field

The disclosure relates generally to an improved computer system and, more specifically, to a method, apparatus, system, and computer program product for estimating a mass of prepared food products through active ultrasonic sensing and information fusion.

2. Description of the Related Art

In the restaurant industry, a weight or mass of prepared food products is an important measure in managing operation of restaurants. The mass of prepared food products can be used in various restaurant operations such as inventory monitoring, waste reporting, ordering, projections, and other operations.

Some types of prepared food products prepared from produce can be difficult to weigh. This difficulty arises from the large volume of produce used, equipment constraints, or other factors.

SUMMARY

According to one embodiment of the present invention, a method estimates a mass of a prepared food product. An ultrasonic beam is steered by a computer system at the prepared food product on a platform. An estimate of a mass of the prepared food product on the platform is determined by the computer system using response signals detected in response to scanning the prepared food product on the platform with the ultrasonic beam.

According to another embodiment of the present invention, a mass estimation system comprises a computer system that steers an ultrasonic beam at a prepared food product on a platform. The computer system determines an estimate of a mass of the prepared food product on the platform using response signals detected in response to scanning the prepared food product on the platform with the ultrasonic beam.

According to yet another embodiment of the present invention, a computer program product for estimating a mass of a prepared food product comprises a computer-readable storage media, first program code and second program code stored on the computer-readable storage media. The first program code is run to steer an ultrasonic beam at the prepared food product on a platform. The second program code is run to determine an estimate of a mass of the prepared food product on the platform using response signals detected in response to scanning the prepared food product on the platform with the ultrasonic beam.

DETAILED DESCRIPTION

Figure 1:
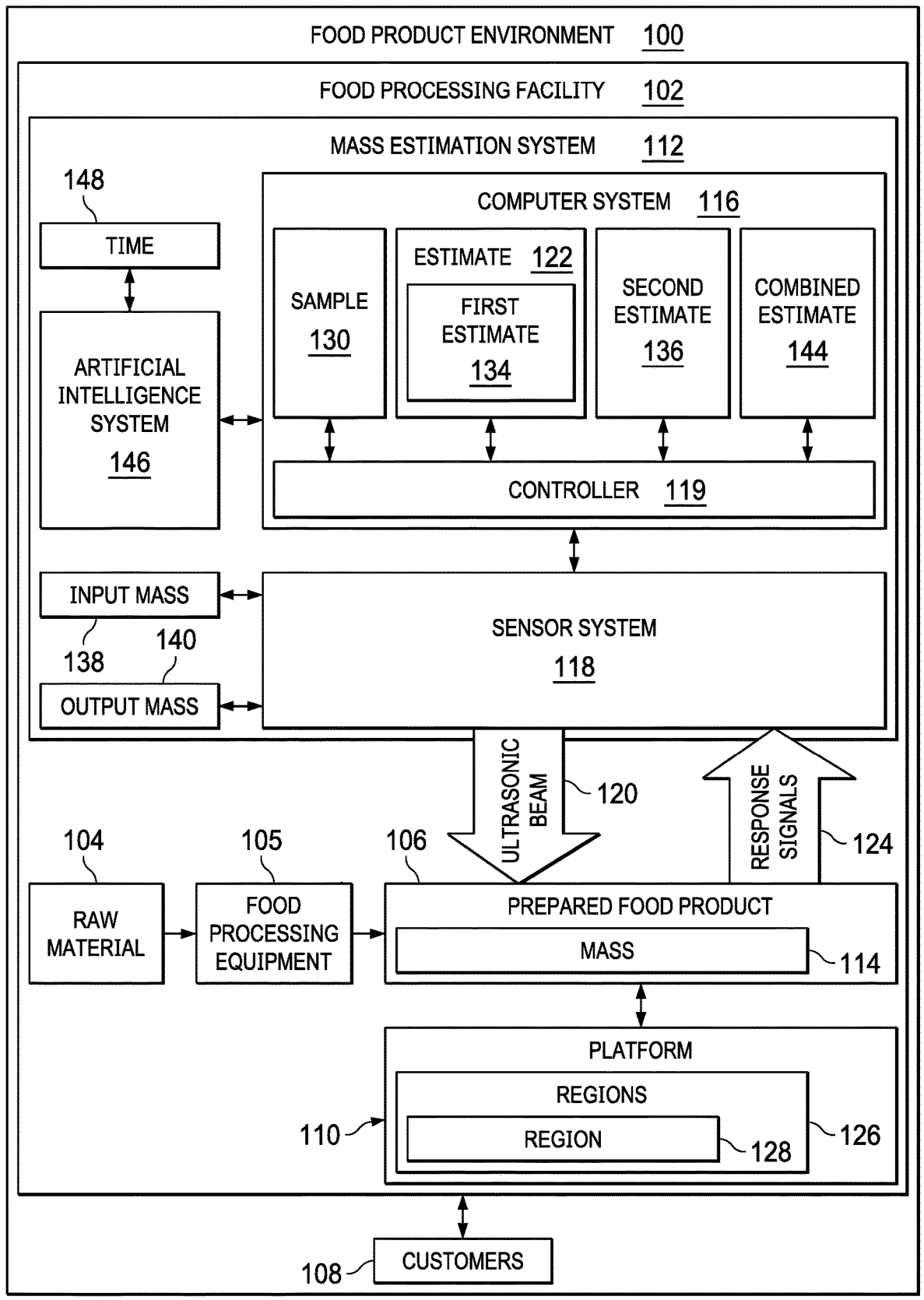
FIG. 1 is a block diagram of a food product environment in accordance with an illustrative embodiment.

The present invention may be a system, a method, and/or a computer program product at any possible technical detail level of integration. The computer program product may include a computer-readable storage medium (or media) having computer-readable program instructions thereon for causing a processor to carry out aspects of the present invention.

The computer-readable storage medium can be a tangible device that can retain and store instructions for use by an instruction execution device. The computer-readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer-readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer-readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer-readable program instructions described herein can be downloaded to respective computing/processing devices from a computer-readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer-readable program instructions from the network and forwards the computer-readable program instructions for storage in a computer-readable storage medium within the respective computing/processing device.

Computer-readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer-readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer-readable program instructions by utilizing state information of the computer-readable program instructions to personalize the electronic circuitry, in order to perform aspects of the present invention.

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer-readable program instructions.

These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer program instructions may also be stored in a computer-readable medium that can direct a computer, other programmable data processing apparatus, or other devices to function in a particular manner, such that the instructions stored in the computer-readable medium produce an article of manufacture including instructions which implement the function/act specified in the flowchart and/or block diagram block or blocks.

The computer-readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be processed substantially concurrently, or the blocks may sometimes be processed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The illustrative embodiments recognize and take into account one or more considerations. For example, the illustrative embodiments recognize and take into account restaurants that cook food products at regular intervals with those prepared food products being sold to meet customer demand. The illustrative embodiments recognize and take into account that accurate measurements of an availability of prepared food products is used to make cooking decisions such as how much raw material to cook and when to cook the raw material to generate the prepared food product. The illustrative embodiments also recognize and take into account that these types of decisions are used to meet the timing of consumer demand while minimizing waste of the prepared food product. Most prepared food products have a short shelf life. As result, the illustrative embodiments recognize and take into account that accurately making decisions on how much and when to prepare food products is important to the operation of a restaurant The illustrative embodiments recognize and take into account that with current restaurant equipment, regular cleaning is needed for the equipment used to hold and handle a prepared food product. For example, with prepared food products that are fried, weight sensors cannot be added to bins for holding the fried prepared food products because of business constraints and cleaning restrictions. As a result, adding the weight sensors to equipment can be infeasible. Further, the illustrative embodiments also recognize and take into account that a mass of prepared food product changes over time as new prepared food product is prepared and existing prepared food product in the bins are sold on a continual basis to customers.

The illustrative embodiments recognize and take into account that, in some cases, infrared sensors can be used. The illustrative embodiments recognize and take into account that with heated bins, heat lamps, and other nearby heat sources, a use of the infrared sensors can be an issue. Further, the illustrative embodiments recognize and take into account that illumination from the heat lamps can reduce the feasibility of using camera-based sensors.

Thus, the illustrative embodiments provide a method, apparatus, system, and computer program product for estimating a mass of a prepared food product. In one illustrative example, a method estimates a mass of a prepared food product. An ultrasonic beam is steered by a computer system at the prepared food product on a platform. An estimate of the mass of the prepared food product on the platform is determined by a computer system using response signals detected in response to scanning the prepared food product on the platform with the ultrasonic beam. This use of the ultrasonic beam is a form of active ultrasonic sensing.

With reference now to the figures and, in particular, with reference to FIG. 1, a block diagram of a food product environment is depicted in accordance with an illustrative embodiment. As depicted, food product environment 100 is an environment in which food processing facility 102 can process raw material 104 to form prepared food product 106 that is sold to customers 108.

In this illustrative example, food processing facility 102 can take a number of different forms. For example, food processing facility 102 can be a restaurant, a cafeteria, a bar, a food truck, a food cart, or some other suitable facility. As used herein, "a number of," when used with reference to items, means one or more items. For example, "a number of different forms" is one or more different forms.

Raw material 104 is any material that can be prepared by food processing equipment 105 to form prepared food product 106 that is sold to customers 108. In this example, food processing equipment 105 can include at least one of an oven, a fryer, a microwave, a mixer, or some other suitable type of equipment. The processing of raw material 104 using food processing equipment 105 to form prepared food product 106 can include at least one of mixing, cutting, grating, heating, frying, microwaving, refrigerating, or freezing of raw material 104. Prepared food product 106 is placed on platform 110 while waiting to be sold to customers 108.

Further, the phrase "at least one of," when used with a list of items, means different combinations of one or more of the listed items can be used, and only one of each item in the list may be needed. In other words, "at least one of" means any combination of items and number of items may be used from the list, but not all of the items in the list are required. Note The item can be a particular object, a thing, or a category.

For example, without limitation, "at least one of item A, item B, or item C" may include item A, item A and item B, or item B. This example also may include item A, item B, and item C or item B and item C. Of course, any combinations of these items can be present. In some illustrative examples, "at least one of" can be, for example, without limitation, two of item A; one of item B; and ten of item C; four of item B and seven of item C; or other suitable combinations.

Raw material 104 can be one or more components. For example, raw material 104 can be selected from at least one of a meat, produce, a vegetable, a fruit, a potato, a popcorn kernel, a sausage link, bread, an egg, a seasoning, a sauce, flour, or some other suitable type of food material. Prepared food product 106 can also take a number of different forms. For example, prepared food product 106 can be selected from a group comprising from at least one of French fries, sausage links, popcorn, green beans, chicken wings, and other suitable types of food products.

In these illustrative examples, prepared food product 106 is placed on platform 110. Platform 110 is a location that holds prepared food product 106 while waiting to be sold to customers 108. Platform 110 can be heated, cooled, room temperature, or some combination thereof depending on the type of prepared food product 106. In this illustrative example, platform 110 can be selected from a group comprising a basket, a bin, a plurality of baskets, and other suitable structures for holding prepared food product 106.

In one illustrative example, raw material 104 can include popcorn kernels placed into a popcorn popper in food processing equipment 105 that heats the popcorn kernels to form popcorn as prepared food product 106. In another illustrative example, raw material 104 can be frozen integrated potatoes, such as frozen tater tots, placed into a fryer in food processing equipment 105 to be prepared by frying to form deep-fried tater tots as prepared food product 106. The tater tots are placed on a heated platform, such as a heated basket.

In yet another illustrative example, corn, tomatoes, jalapeno peppers, salt, cilantro, and lime are raw material 104 to be prepared by mixing the ingredients in a mixer in food processing equipment 105 to form a corn salsa as prepared food product 106. Corn salsa is placed on a chilled or cooled platform, such as a cooled pan.

In this illustrative example, knowing or estimating an amount of prepared food product 106 on platform 110 is used to determine when and how much of raw material 104 is to be prepared to prepare additional amounts of prepared food product 106. This additional prepared food is placed on platform 110 for sale to customers 108.

As depicted, prepared food product 106 has a limited life span on platform 110. At some point in time, unsold portions of prepared food product 106 on platform 110 are discarded when prepared food product 106 is no longer considered suitable for sale to customers 108.

The amount of time that prepared food product 106 remains suitable for sale to customers 108 varies based on the type of prepared food product 106. For example, the life span of a hamburger is 20 minutes, French fries are 7 minutes, a sausage link is one hour, and popcorn is two hours. The lifespan of a particular type of prepared food product 106 can be determined based on a number of different factors.

The decision on when a particular type of prepared food product 106 is discarded can be based on one or more factors including at least one of freshness, temperature, dryness, spoilage, or other factors for food quality. Often, prepared food product 106 is considered no longer suitable for customers 108 even though prepared food product 106 is not considered spoiled. The appeal and taste to customers 108 is often a deciding factor.

In this illustrative example, mass estimation system 112 operates to estimate mass 114 of prepared food product 106 located on platform 110. Mass estimation system 112 includes a number of different components. In this illustrative example, mass estimation system 112 includes computer system 116 and sensor system 118.

Computer system 116 is a physical hardware system and includes one or more data processing systems. When more than one data processing system is present in computer system 116, those data processing systems are in communication with each other using a communications medium. The communications medium can be a network. The data processing systems can be selected from at least one of a computer, a server computer, a tablet computer, or some other suitable data processing system.

Controller 119 in computer system 116 steers ultrasonic beam 120 at prepared food product 106 on platform 110. In this illustrative example, ultrasonic beam 120 is emitted from sensor system 118, which is a physical hardware system controlled by computer system 116. Ultrasonic beam 120 comprises sound that is emitted in the form of a beam. Ultrasonic beam 120 comprises sound at frequencies greater than the upper audible limit of human hearing. For example, ultrasonic beam 120 can comprise sound at frequencies greater than 20 KHz.

As depicted, controller 119 in computer system 116 determines estimate 122 of mass 114 of prepared food product 106 on platform 110 using response signals 124 detected in response to scanning prepared food product 106 on platform 110 with ultrasonic beam 120. In this illustraexample, response signals 124 are sound signals from reflections of the sound in ultrasonic beam 120 encountering prepared food product 106.

As depicted, the steering of ultrasonic beam 120 by controller 119 causes ultrasonic beam 120 to move with respect to prepared food product 106 in a manner that ultrasonic beam 120 scans prepared food product 106. This scanning can be performed in a number of different ways.

For example, controller 119 in computer system 116 can select a set of regions 126 on platform 110 with prepared food product 106 for scanning. As used herein, "a set of," when used with reference to items, means one or more items. For example, "a set of regions 126" is one or more regions in regions 126. The set of regions 126 can cover all or a portion of platform 110. For example, the set of regions 126 can be selected to cover the portion of platform 110 on which prepared food product 106 is present.

Further, the set of regions 126 can have different shapes. For example, the set of regions 126 can have a shape selected from at least one of a square, a rectangle, a hexagon, or some other two-dimensional suitable shape.

In this illustrative example, controller 119 selects the set of regions 126 on platform 110 using a Monte Carlo method. A Monte Carlo method is a computational process that relies on repeated sampling to obtain numerical results. This process is used in this example to select the set of regions 126 for sampling. The Monte Carlo method is used to identify at least one of which region should be selected as part of the set of regions 126 or the size of a region in the set of regions 126.

As depicted, controller 119 in computer system 116 scans the set of regions 126 with ultrasonic beam 120 to scan prepared food product 106. Controller 119 detects response signals 124 for region 128 in the set of regions 126 using sensor system 118 to form sample 130 of mass 114 for region 128. In this illustrative example, controller 119 repeats scanning of region 128 in the set of regions 126 to scan prepared food product 106 and detecting response signals 124 for region 128 in the set of regions 126 to form an updated sample for region 128 with at least one of a different diameter or angle for ultrasonic beam 120 until sample 130 of mass 114 for region 128 converges by a desired amount.

In this illustrative example, the angle of ultrasonic beam 120 is the angle at which ultrasonic beam 120 encounters prepared food product 106. For example, when ultrasonic beam 120 is emitted directly from sensor system 118 straight down onto prepared food product 106, the angle is zero degrees. As ultrasonic beam 120 is steered to other portions of prepared food product 106, a different angle is present. This angle also can be changed by changing the manner in which ultrasonic beam 120 is emitted from sensor system 118. For example, the location in sensor system 118 from which ultrasonic beam 120 is emitted can be changed. As a result, the location at which the angle was zero degrees in a prior scan of prepared food product 106 is now a different angle from zero degrees. This type of angle perturbation can be used to obtain a more accurate estimate of mass 114.

In another illustrative example, estimate 122 is first estimate 134. Controller 119 in computer system 116 determines second estimate 136 of mass 114 of prepared food product 106 on platform 110 using input mass 138 of raw material 104 used to prepare prepared food product 106 and output mass 140 of prepared food product 106 sold to customers 108.

Input mass 138 is the mass of raw material 104 that is prepared by food processing equipment 105 to form prepared food product 106. The value of input mass 138 may not equal mass 114 of prepared food product 106. Mass 114 of prepared food product 106 resulting from input mass 138 is known in this example. This relationship can be used by controller 119 to determine mass 114 of prepared food product 106 resulting from processing raw material 104. Depending on the desired accuracy, the difference between input mass 138 and output mass 140 can be second estimate 136 of mass 114 of prepared food product 106 in some illustrative examples.

Output mass 140 can be determined in a number of different ways. For example, prepared food product 106 can be packaged when sold to customers 108. An estimate of the amount of prepared food product 106 can be determined based on the packaging used. The sale of prepared food product 106 in this packaging can be identified based on detecting a sale to customers 108.

In this illustrative example, prepared food product 106 in packaging, but not sold to customers 108, can be considered part of prepared food product 106 on platform 110. In this depicted example, platform 110 can include a bin in which prepared food product 106 is placed and a basket or some other structure in which prepared food product 106 in packaging is placed when not yet sold to customers 108. This basket or other structure can be scanned by ultrasonic beam 120 as part of scanning of the unpackaged prepared food product when scanning platform 110.

As depicted, controller 119 in computer system 116 combines first estimate 134 of mass 114 of prepared food product 106 and second estimate 136 of mass 114 of prepared food product 106 to form combined estimate 144 of mass 114 of prepared food product 106. Combining first estimate 134 and second estimate 136 is a fusion of these estimates. This fusion of first estimate 134 and second estimate 136 by controller 119 to form combined estimate 144 can result in an increase in the accuracy of the estimate of mass 114 as compared to only using first estimate 134 or second estimate 136.

Further, artificial intelligence system 146 can be present in computer system 116. Artificial intelligence system 146 is a system that has intelligent behavior and can be based on function of a human brain. An artificial intelligence system comprises at least one of an artificial neural network, a cognitive system, a Bayesian network, a fuzzy logic, an expert system, a natural language system, a cognitive system, or some other suitable system. Machine learning is used to train the artificial intelligence system. Machine learning involves inputting data to the process and allowing the process to adjust and improve the function of artificial intelligence system 146.

In this illustrative example, artificial intelligence system 146 can determine second estimate 136 of mass 114 of prepared food product 106 using input mass 138 of raw material 104 used to prepare prepared food product 106, output mass 140 of prepared food product 106 sold, and time 148 as inputs into artificial intelligence system 146.

Controller 119 can be implemented in software, hardware, firmware, or a combination thereof. When software is used, the operations performed by controller 119 can be implemented in program code configured to run on hardware, such as a processor unit. When firmware is used, the operations performed by controller 119 can be implemented in program code and data and stored in persistent memory to run on a processor unit. When hardware is employed, the hardware may include circuits that operate to perform the operations in controller 119.

In the illustrative examples, the hardware may take a form selected from at least one of a circuit system, an integrated circuit, an application-specific integrated circuit (ASIC), a programmable logic device, or some other suitable type of hardware configured to perform a number of operations. With a programmable logic device, the device can be configured to perform the number of operations. The device can be reconfigured at a later time or can be permanently configured to perform the number of operations. Programmable logic devices include, for example, a programmable logic array, a programmable array logic, a field programmable logic array, a field programmable gate array, and other suitable hardware devices. Additionally, the processes can be implemented in organic components integrated with inorganic components and can be comprised entirely of organic components excluding a human being. For example, the processes can be implemented as circuits in organic semiconductors.

In one illustrative example, one or more technical solutions are present that overcome a technical problem with estimating mass 114 of prepared food product 106 with increased accuracy for use in managing the operation of food processing facility 102. As a result, one or more technical solutions can provide a technical effect of increasing accuracy in estimating mass 114 of prepared food product 106 using ultrasonic beam 120 to obtain the data needed to generate estimate 122 of mass 114 of prepared food product 106. Additionally, one or more technical solutions can provide an ability to increase the accuracy in estimating mass 114 of prepared food product 106 through also determining second estimate 136 of mass 114 of prepared food product 106 in which first estimate 134 and second estimate 136 are combined to form combined estimate 144 of mass 114 of prepared food product 106.

Further, one or more technical solutions enable estimating mass 114 of prepared food product 106 on platform 110 without physical contact with sensors in sensor system 118. Still further, one or more technical solutions enable avoiding issues with heat lamps and heat encountered through current measurement systems by using ultrasonic beam 120 to obtain data used in estimating mass 114 of prepared food product 106.

Computer system 116 can be configured to perform at least one of the steps, operations, or actions described in the different illustrative examples using software, hardware, firmware, or a combination thereof. As a result, computer system 116 operates as a special purpose computer system in which controller 119 in computer system 116 enables directing ultrasonic beam 120 in a manner that causes response signals 124 that are detected through sensor system 118 in a manner to generate data for determining at least one of first estimate 134, second estimate 136, or combined estimate 144 of mass 114 of prepared food product 106. In particular, controller 119 transforms computer system 116 into a special purpose computer system as compared to currently available general computer systems that do not have controller 119.

Figure 2:
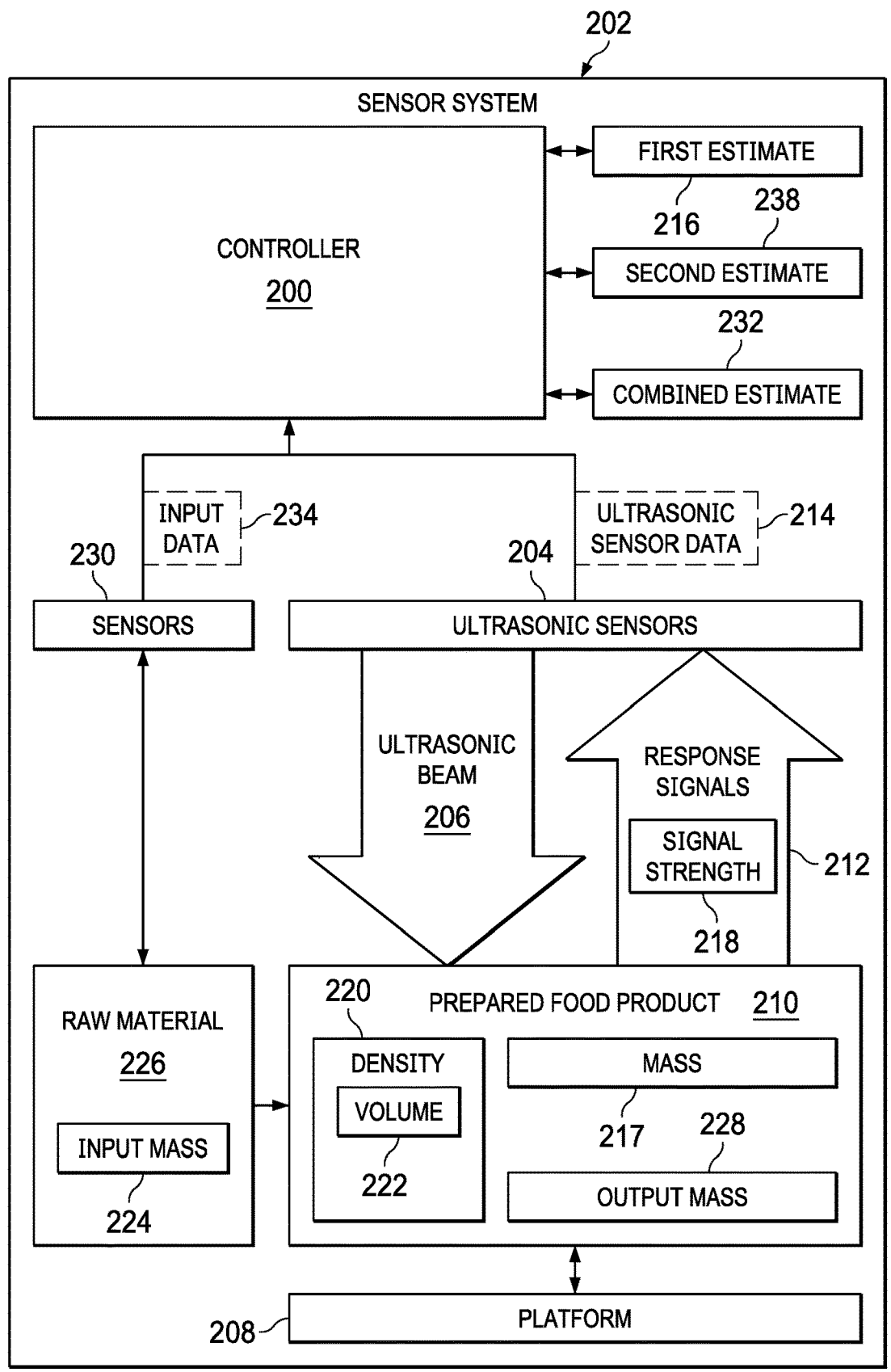
FIG. 2 is a diagram illustrating data flow in estimating a mass of a prepared food product in accordance with an illustrative embodiment.

With reference to FIG. 2, a diagram illustrating data flow in estimating a mass of a prepared food product is depicted in accordance with an illustrative embodiment. In this illustrative example, controller 200 is an example of one implementation for controller 119 in computer system 116 in FIG. 1.

As depicted, controller 200 determines mass 217 of prepared food product 210 using density 220 and volume 222 of prepared food product 210. In one illustrative example, prepared food product 210 takes the form of popcorn.

In this illustrative example, density 220 and volume 222 are determined using sensor system 202. Angle perturbation of ultrasonic beam 206 can occur through changing the location from which ultrasonic beam 206 is emitted from the array of ultrasonic sensors 204. This angle perturbation can be used to obtain additional samples of data to increase the accuracy in determining at least one of density 220 or volume 222.

Controller 200 is in communication with sensor system 202. Sensor system 202 is a physical sensor system and is one example of an implementation for sensor system 118 in FIG. 1. As depicted, sensor system 202 includes an array of ultrasonic sensors 204. The array of ultrasonic sensors 204 can also be referred to as an array of ultrasonic transducers.

The array of ultrasonic sensors 204 can include transmitters that transmit sound and receivers that detect sound. The array of ultrasonic sensors 204 also can include transceivers that both transmit and detect sound. Ultrasonic beam 206 is emitted from the array of ultrasonic sensors 204.

As depicted, ultrasonic beam 206 can be formed by controlling a phase and relative amplitude of each transmitter or transceiver in the array of ultrasonic sensors 204. Further, steering can also be performed electronically by controlling the phase and amplitude of each transmitter or transceiver in the array of ultrasonic sensors 204.

The array of ultrasonic sensors 204 is located over platform 208 on which prepared food product 210 is located. The location of the array of ultrasonic sensors 204 is selected in a manner that ultrasonic beam 206 can be steered to scan prepared food product 210. Further, the array of ultrasonic sensors 204 does not need to be located directly over or parallel to platform 208. Response signals 212 are detected by the array of ultrasonic sensors 204 in response to ultrasonic beam 206 being directed to prepared food product 210.

As depicted, ultrasonic sensor data 214 is sent from sensor system 202 to controller 200. Signal strength 218 in ultrasonic sensor data 214 is used to determine density 220 and volume 222 for prepared food product 210. Density 220 and volume 222 are used to determine first estimate 216 of mass 217 of prepared food product 210. In this illustrative example, first estimate 216 is determined as density 220 of prepared food product 210 multiplied by volume 222 of prepared food product 210.

As depicted, controller 200 determines density 220 of prepared food product 210 from a variance in signal strength 218 of response signals 212 in ultrasonic sensor data 214. Density 220 is the mass of food per unit volume. For example, density 220 can be grams/cm$^3$. Increased variation in signal strength 218 indicates a lower value for density 220 as compared to less variation in signal strength 218.

In one example, the estimate of density 220 based on the variation in signal strength 218 can be determined from a table of signal strength variations and densities. The table can be generated from empirical data in which variations in signal strengths have been detected for known densities of prepared food product 210. For example, when prepared food product 210 takes the form of popcorn, the popcorn can be scanned on platform 208 to identify variations in signal strength 218 for known densities of the popcorn on platform 208. These measurements can be used to create the table.

In this illustrative example, controller 200 also determines volume 222 of prepared food product 210 from a maximum value of signal strength 218 in response signals 212 detected in ultrasonic sensor data 214. As depicted, volume 222 is determined by controller 200 using a height measured for prepared food product 210 and an area of platform 208 in which prepared food product 210 is present.

A maximum value of signal strength 218 in ultrasonic sensor data 214 can be used to identify the height of prepared food product 210 on platform 208. A table can also be used to determine the height based on signal strength 218. This table can also be created from empirical data generated by measuring the maximum value of signal strength 218 for known heights of prepared food product 210. Further, with the dimensions of platform 208, the area of platform 208 can be determined.

In the illustrative example, the height and area can be used to determine volume 222 of prepared food product 210 when prepared food product 210 covers platform 208. In this illustrative example, a table of heights and signal strength values can be used to identify height of prepared food product 210. This table can be generated from the empirical data measuring the maximum value signal strengths for the known heights of prepared food product 210. When prepared food product 210 is popcorn, measurements of signal strength values can be made of popcorn with known heights.

In some illustrative examples, prepared food product 210 may not cover all of platform 208, the height of prepared food product 210 varies, or both prepared food product 210 does not cover all of platform 208 and the height of prepared food product 210 varies. For example, when prepared food product 210 is popcorn, piles or mounds of popcorn may be present on platform 208.

In this example, regions can be used to determine volume 222. The height can be determined for the regions in which prepared food product 210 is present on platform 208. Each region can be selected to include a portion of prepared food product 210 that has substantially the same height or within some tolerance. For example, one region can include a pile, while another region includes a lower area.

For each region, controller 200 uses the maximum value of signal strength 218 to determine the height within the region. This height determination can be used to determine the volume for each region. Controller 200 aggregates the volumes of the regions to identify volume 222 of prepared food product 210.

In other illustrative examples, the time-of-flight or the time after which a response signal is received in response to ultrasonic beam 206 can be used to determine the height of prepared food product 210. A shorter time indicates a greater value for the height as compared to a longer time.

Controller 200 determines second estimate 238 of density 220 for prepared food product 210 from input mass 224 of raw material 226 and output mass 228 of prepared food product 210. In this illustrative example, input mass 224 of raw material 226 can be determined using input data 234 from a number of sensors 230 in sensor system 202. For example, a camera in the number of sensors 230 can generate images of raw material 226. These images can be analyzed to estimate input mass 224.

As another example, a position sensor in the number of sensors 230 at a valve that deposits raw material 226 into food processing equipment can be used to determine input mass 224. For example, each actuation of the valve can input a set amount of raw material 226. Thus, detecting the number of actuations of the valve can be used to determine input mass 224. In another example, different valves may input different amounts of raw material 226. Detecting which valves are actuated can be used to determine input mass 224.

In yet other illustrative examples, the number of sensors 230 can be used to detect the activation of the food processing equipment. If a predetermined amount of raw material 226 is used each time the food processing equipment is activated, input mass 224 can also be determined from detecting activation of the food processing equipment by the number of sensors 230 to detect the input of the predetermined amount of raw material 226.

As depicted, controller 200 can use sensor system 202 to detect sales of prepared food product 210 in output data 236, which can be used to determine output mass 228 of prepared food product 210. For example, sensor system 202 can include point of sale (POS) devices used to sell prepared food product 210. In this example, the number of units of prepared food product 210 detected by sensor system 202 can be sent as output data 236 to controller 200 for use in determining output mass 228. The unit of prepared food product 210 can have a known mass. Although this mass can vary between units, the mass can be estimated. For example, when prepared food product 210 is popcorn, the units be at least one of a bag, a cup, a bucket, or some other suitable packaging or structure.

If the units can have different sizes, the mass of each of those sizes are known in these examples. In this manner, output mass 228 can be determined from output data 236. In another example, output mass 228 can be determined if prepared food product 210 is sold by weight. With this example, prepared food product 210 can be weighed prior to being sold. This weight can be sent in output data 236 to controller 200.

With first estimate 216 of mass 217 for prepared food product 210 and second estimate 238 of mass 217 for prepared food product 210, controller 200 can determine combined estimate 232 of mass 217 for prepared food product 210.

The illustrations of food product environment 100 in FIG. 1 and controller 200 and sensor system 202 in FIG. 2 are not meant to imply physical or architectural limitations to the manner in which an illustrative embodiment can be implemented. Other components in addition to or in place of the ones illustrated may be used. Some components may be unnecessary. Also, the blocks are presented to illustrate some functional components. One or more of these blocks may be combined, divided, or combined and divided into different blocks when implemented in an illustrative embodiment.

For example, a selection of a set of regions 126 can be made using other techniques in addition to or in place of a Monte Carlo method. For example, the set of regions 126 can be selected based on the type of prepared food product 106, the uniformity of prepared food product 106 on platform 110, or other suitable factors. This type of selection can be made using a policy, which is a set of rules that identify the set of regions 126 based on various factors such as the type of prepared food product 106, the uniformity of prepared food product 106 on platform 110, or other suitable factors.

Further, although artificial intelligence system 146 is shown as a separate component from controller 119 in FIG. 1, this component can be implemented as part of controller 119 in some illustrative examples. As another example, computer system 116 is shown as being located within food processing facility 102. In some illustrative examples, a portion or all of computer system 116 can be in a location that is remote to food processing facility 102.

In illustrative examples, mass estimation system 112 can be used to determine the mass of all types for processed food products. Mass estimation system 112 can be especially useful in estimating the mass of processed food products with variable packing density. Further, these types of processed food products can exhibit large variations in volume depending on how the processed food products are placed on platforms, such as bins or baskets.

Figure 3:
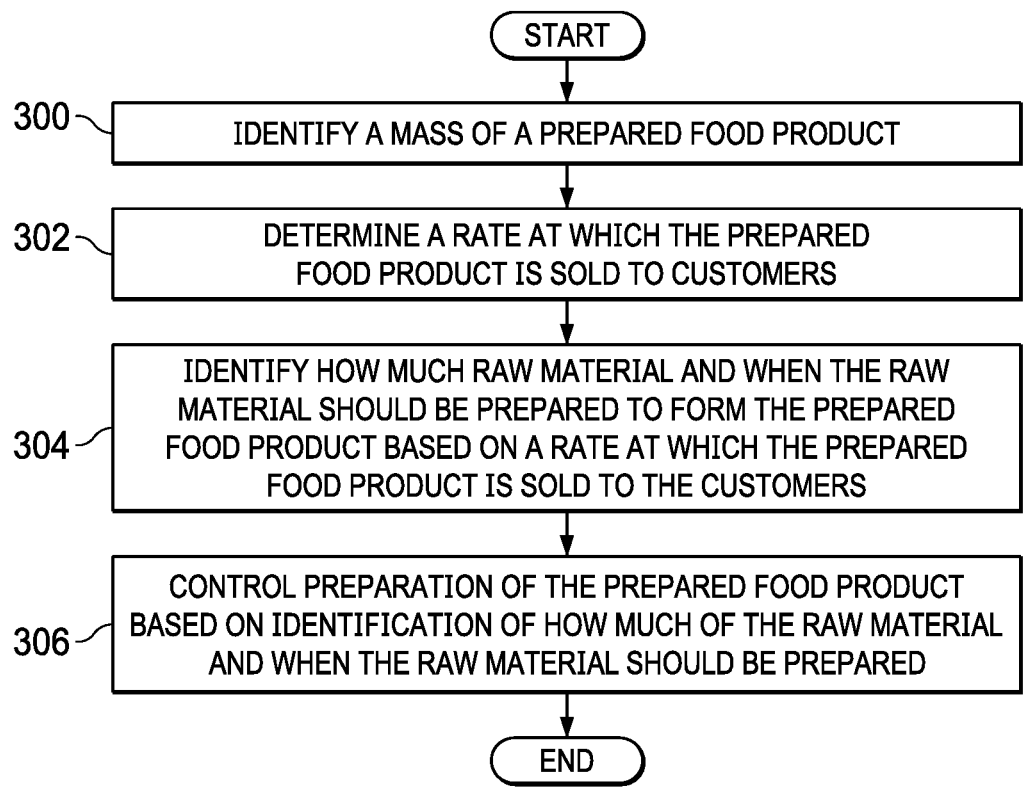
FIG. 3 is a flowchart of a process controlling preparation of a prepared food product in accordance with an illustrative embodiment.

With reference next to FIG. 3, a flowchart of a process controlling preparation of a prepared food product is depicted in accordance with an illustrative embodiment. The processes in FIG. 3 can be implemented in hardware, software, or both. When implemented in software, the processes can take the form of program code that is run by one of more processor units located in one or more hardware devices in one or more computer systems. For example, these processes can be implemented in controller 119 in computer system 116 in FIG. 1. This process can be used to control at least one of when or how much raw material 104 is prepared using food processing equipment 105 to create prepared food product 106 for sale to customers 108.

The process begins by identifying a mass of a prepared food product (step 300). This mass can be for a particular type of food product on one or more platforms in a food processing facility.

The process determines a rate at which the prepared food product is sold to customers (step 302). In step 302, the rate can be determined based on sales made to the customers. Further, this rate can include projections of sales. In the illustrative example, these projections can be determined using an artificial intelligence system, an expert system, or other process that uses historical sales information or other information to predict future sales of the prepared food product.

The process identifies how much raw material and when the raw material should be prepared to form the prepared food product based on a rate at which the prepared food product is sold to the customers (step 304). This identification is made to have sufficient amounts of prepared food product available for sale based on predicted sales of the prepared food product. This increase takes into account having sufficient prepared food product available for the customers when demand is present. Further, the increase also takes into account having an amount of the prepared food product available that reduces waste from having to discard the prepared food product.

The process controls preparation of the prepared food product based on identification of how much of the raw material and when the raw material should be prepared (step 306). The process terminates thereafter.

Figure 4:
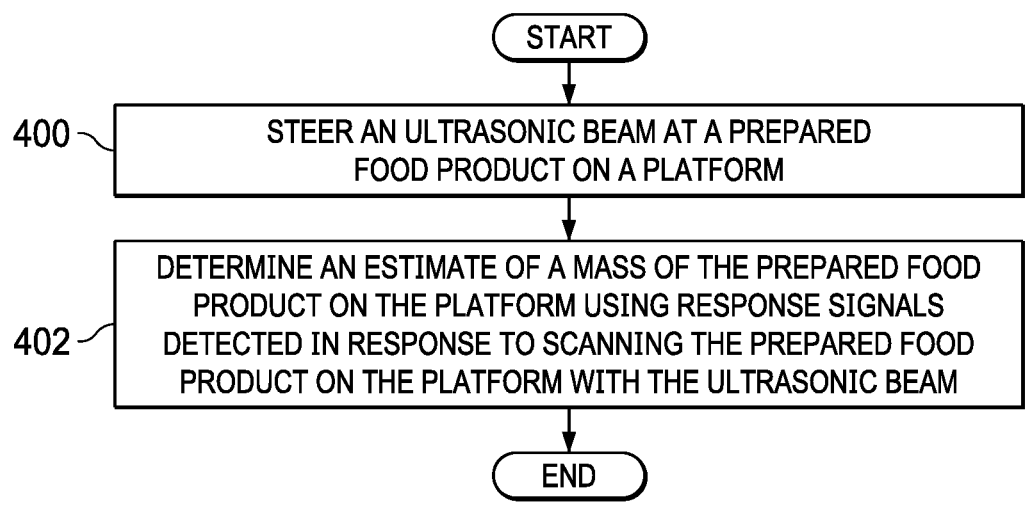
FIG. 4 is a flowchart of a process for estimating a mass of a prepared food product in accordance with an illustrative embodiment.

Turning next to FIG. 4, a flowchart of a process for estimating a mass of a prepared food product is depicted in accordance with an illustrative embodiment. The processes in FIG. 4 can be implemented in hardware, software, or both. When implemented in software, the processes can take the form of program code that is run by one of more processor units located in one or more hardware devices in one or more computer systems. For example, these processes can be implemented in controller 119 in computer system 116 in FIG. 1. This process is an example of one implementation of step 300 in FIG. 3.

The process begins by steering an ultrasonic beam at a prepared food product on a platform (step 400). The process determines an estimate of a mass of the prepared food product on the platform using response signals detected in response to scanning the prepared food product on the platform with the ultrasonic beam (step 402). The process terminates thereafter.

Figure 5:
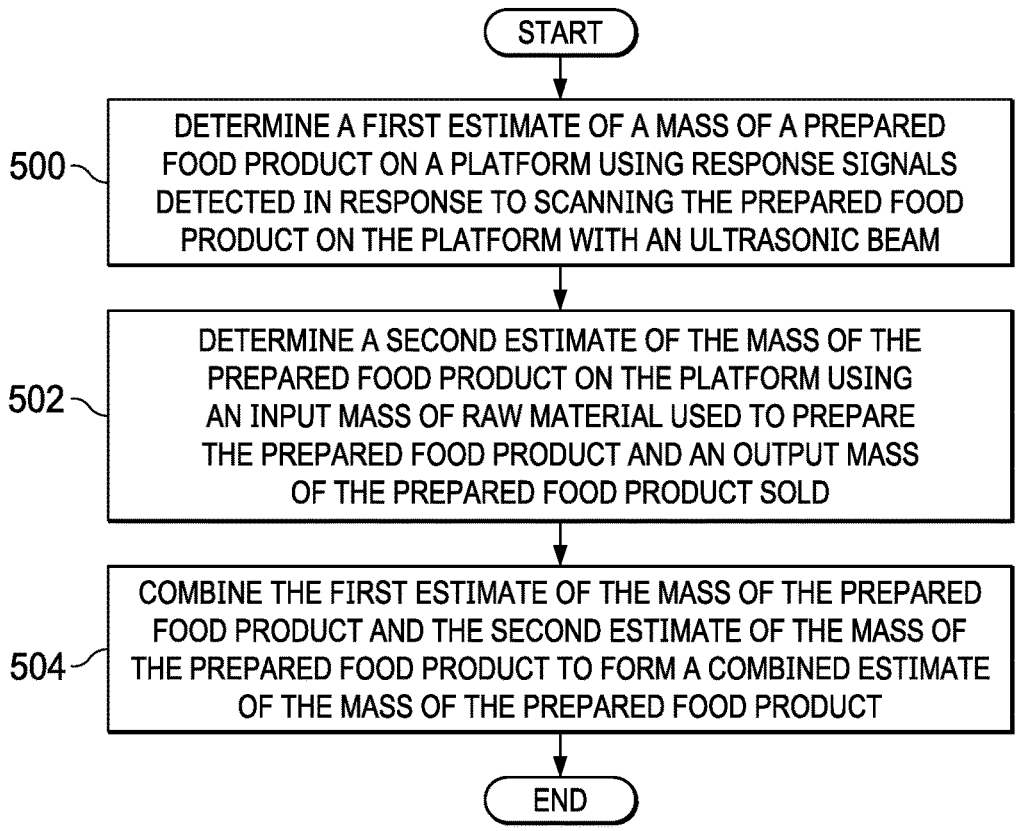
FIG. 5 is another flowchart of a process for estimating a mass of a prepared food product in accordance with an illustrative embodiment.

With reference next to FIG. 5, another flowchart of a process for estimating a mass of a prepared food product is depicted in accordance with an illustrative embodiment. The processes in FIG. 5 can be implemented in hardware, software, or both. When implemented in software, the processes can take the form of program code that is run by one of more processor units located in one or more hardware devices in one or more computer systems. For example, these processes can be implemented in controller 119 in computer system 116 in FIG. 1. This process in this flowchart is an example of one implementation of step 300 in FIG. 3.

The process begins by determining a first estimate of a mass of a prepared food product on a platform using response signals detected in response to scanning the prepared food product on the platform with an ultrasonic beam (step 500). The process determines a second estimate of the mass of the prepared food product on the platform using an input mass of raw material used to prepare the prepared food product and an output mass of the prepared food product sold (step 502).

The process combines the first estimate of the mass of the prepared food product and the second estimate of the mass of the prepared food product to form a combined estimate of the mass of the prepared food product (step 504). The process terminates thereafter. Step 504 is a fusion of the two estimates. This fusion can enable determining a more accurate estimate of the mass of the prepared food product.

Figure 6:
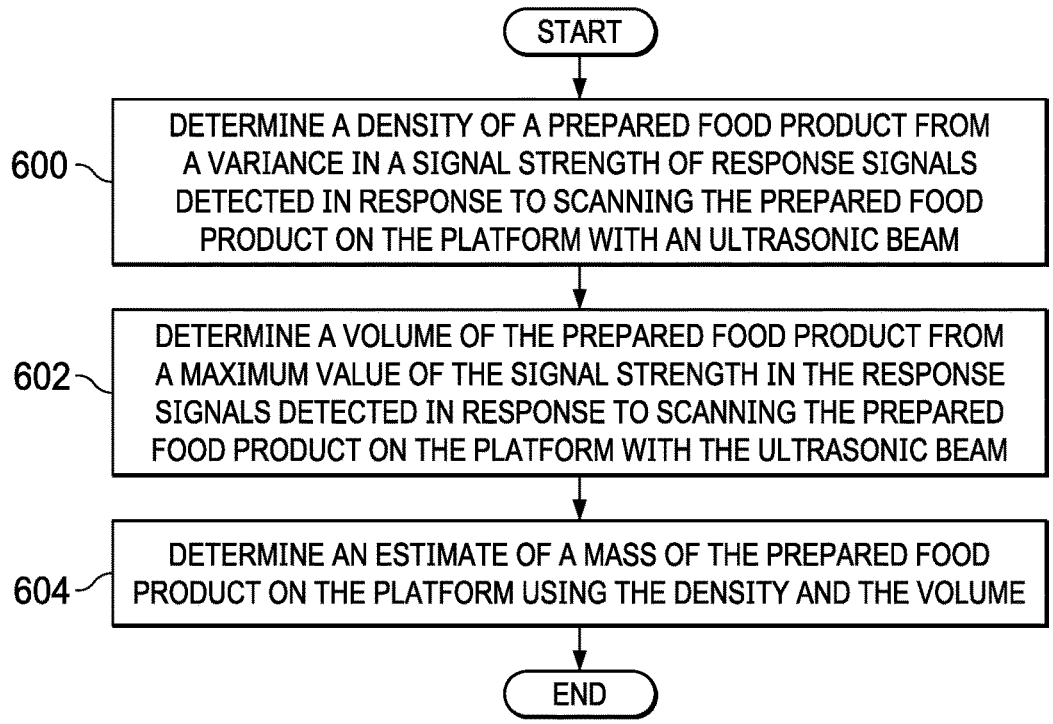
FIG. 6 is a flowchart of a process for determining a first estimate of a mass of prepared food product using an ultrasonic beam in accordance with an illustrative embodiment.

Turning next to FIG. 6, a flowchart of a process for determining a first estimate of a mass of a prepared food product using an ultrasonic beam is depicted in accordance with an illustrative embodiment. In FIG. 6, the process is an example of one implementation for estimating the mass of a prepared food product in step 402 in FIG. 4. This process in this flowchart in FIG. 6 also is an example of one implementation for step 500 in FIG. 5.

The process begins by determining a density of a prepared food product from a variance in a signal strength of response signals detected in response to scanning the prepared food product on a platform with an ultrasonic beam (step 600). In step 600, the density is the amount of prepared food product per unit volume. For example, the density can be $gm/cm^3$. Increased variation in signal strength indicates less density as compared to less variation in the signal strength.

The process determines a volume of the prepared food product from a maximum value of the signal strength in the response signals detected in response to scanning the prepared food product on the platform with the ultrasonic beam (step 602). In this illustrative example, the maximum value of the signal strength can be used to identify a height of the prepared food product on the platform. Further, when the dimensions of the platform are known, the height and area can be used to identify the volume of the prepared food product.

The process determines an estimate of a mass of the prepared food product on the platform using the density and the volume (step 604). The process terminates thereafter.

Figure 7:
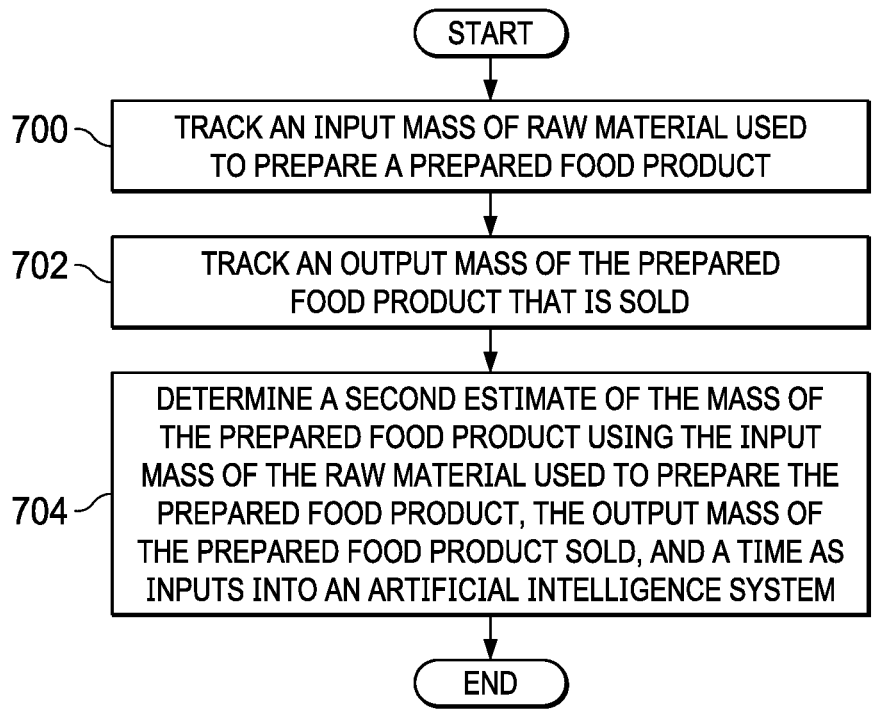
FIG. 7 is a flowchart of a process for determining a second estimate of a mass of a prepared food product in accordance with an illustrative embodiment.

In FIG. 7, a flowchart of a process for determining a second estimate of a mass of a prepared food product is depicted in accordance with an illustrative embodiment. The process in this figure is an example of an implementation for step 502 in FIG. 5.

The process begins by tracking an input mass of raw material used to prepare a prepared food product (step 700). The process tracks an output mass of the prepared food product that is sold (step 702).

The process determines a second estimate of the mass of the prepared food product using the input mass of the raw material used to prepare the prepared food product, the output mass of the prepared food product sold, and a time as inputs into an artificial intelligence system (step 704). The process terminates thereafter.

In step 704, the determination of the second estimate can be performed using an artificial intelligence system, an expert system, a table, or some other suitable mechanism. In this illustrative example, the artificial intelligence system can be trained through machine learning to determine the second estimate in a more accurate manner. For example, the artificial intelligence system can determine the mass of the prepared food product resulting from the input mass of the raw material.

Additionally, the artificial intelligence system can take into account that portions of the prepared food product may be discarded without being sold. These different factors can be taken into account through machine learning using the input mass and the output mass with actual measurements of mass for the prepared food product. For example, an amount of the prepared food product being discarded can vary depending on a time of day, a day of week, a month, or other time factors such as holidays. Further, the amount of the prepared food product being discarded can also vary depending on who is preparing the prepared food product. These and other factors may be taken into account by the artificial intelligence system through machine learning.

Figure 8:
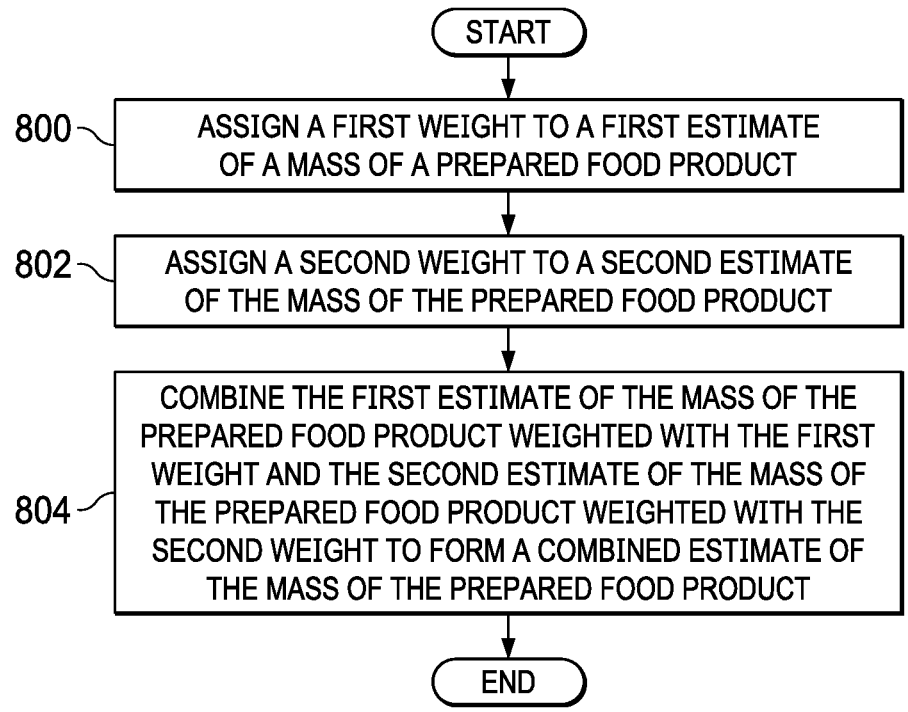
FIG. 8 is a flowchart of a process for combining a first estimate of a mass for a prepared food product and a second estimate of the mass of the prepared food product in accordance with an illustrative embodiment.

Turning next to FIG. 8, a flowchart of a process for combining a first estimate of a mass for a prepared food product and a second estimate of the mass of the prepared food product is depicted in accordance with an illustrative embodiment. The process in this flowchart is an example of one implementation for step 504 in FIG. 5.

The process begins by assigning a first weight to a first estimate of a mass of a prepared food product (step 800). The process assigns a second weight to a second estimate of the mass of the prepared food product (step 802). In step 800 and step 802, the assignment of weights can be performed in a number of different ways. For example, an artificial intelligence system can assign these weights. The artificial intelligence system can be trained to identify which estimate is more accurate for different times. The time is for a time of day and can also include a day of a week, a day of a month, or other additional date parameters. Machine training of the artificial intelligence system can be performed to train the artificial intelligence system to identify which estimates are more accurate. The estimate with a greater accuracy for the time is assigned a greater weight in this illustrative example.

The process combines the first estimate of the mass of the prepared food product weighted with the first weight and the second estimate of the mass of the prepared food product weighted with the second weight to form a combined estimate of the mass of the prepared food product (step 804). The process terminates thereafter.

The flowcharts and block diagrams in the different depicted embodiments illustrate the architecture, functionality, and operation of some possible implementations of apparatuses and methods in an illustrative embodiment. In this regard, each block in the flowcharts or block diagrams may represent at least one of a module, a segment, a function, or a portion of an operation or step. For example, one or more of the blocks can be implemented as program code, hardware, or a combination of the program code and hardware. When implemented in hardware, the hardware may, for example, take the form of integrated circuits that are manufactured or configured to perform one or more operations in the flowcharts or block diagrams. When implemented as a combination of program code and hardware, the implementation may take the form of firmware. Each block in the flowcharts or the block diagrams can be implemented using special purpose hardware systems that perform the different operations or combinations of special purpose hardware and program code run by the special purpose hardware.

In some alternative implementations of an illustrative embodiment, the function or functions noted in the blocks may occur out of the order noted in the figures. For example, in some cases, two blocks shown in succession can be performed substantially concurrently, or the blocks may sometimes be performed in the reverse order, depending upon the functionality involved. Also, other blocks can be added in addition to the illustrated blocks in a flowchart or block diagram.

Figure 9:
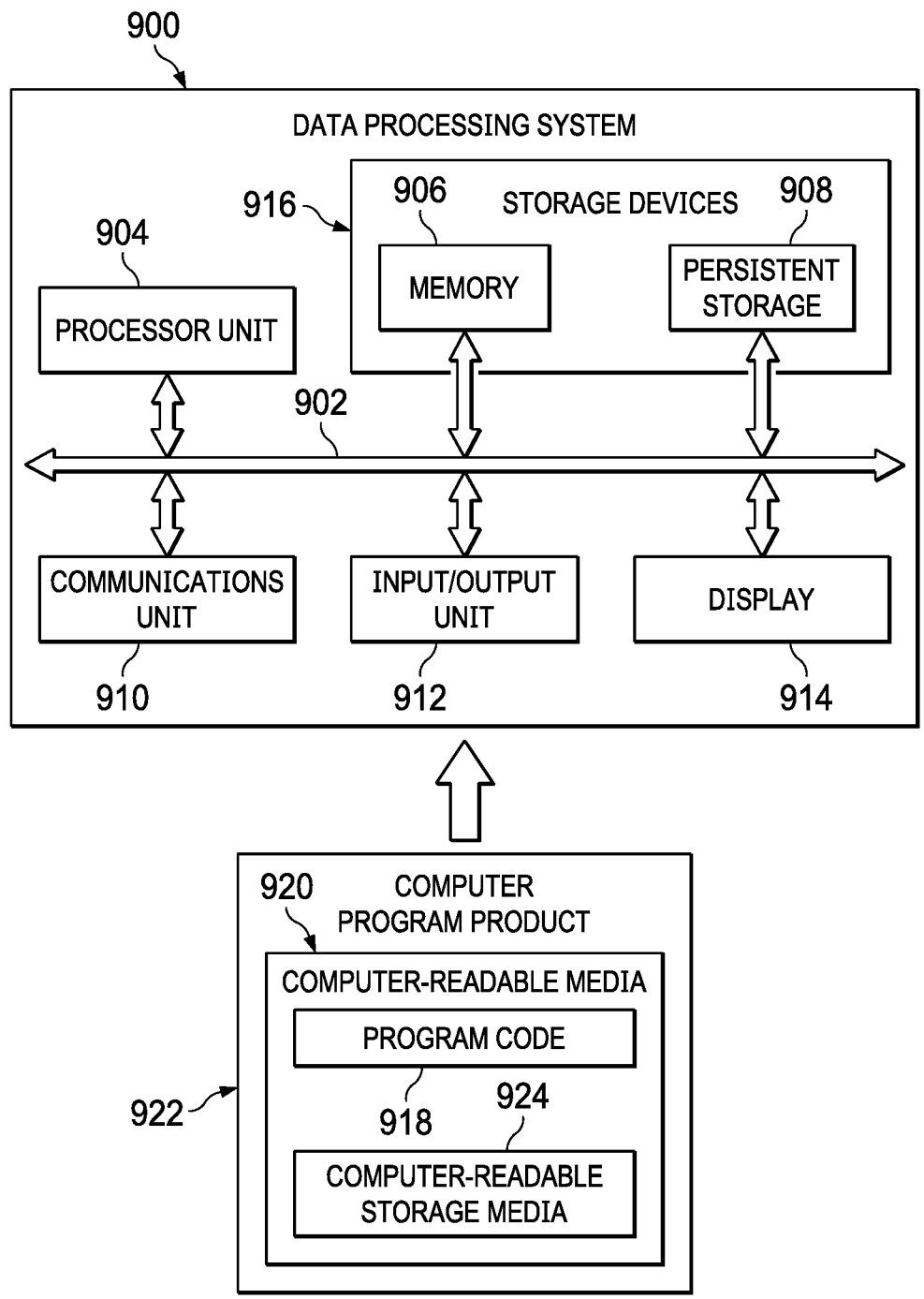
FIG. 9 is a block diagram of a data processing system in accordance with an illustrative embodiment.

Turning now to FIG. 9, a block diagram of a data processing system is depicted in accordance with an illustrative embodiment. Data processing system 900 can be used to implement computer system 116 in FIG. 1. In this illustrative example, data processing system 900 includes communications framework 902, which provides communications between processor unit 904, memory 906, persistent storage 908, communications unit 910, input/output (I/O) unit 912, and display 914. In this example, communications framework 902 takes the form of a bus system.

Processor unit 904 serves to execute instructions for software that can be loaded into memory 906. Processor unit 904 include one or more processors. For example, processor unit 904 can be selected from at least one of a multicore processor, a central processing unit (CPU), a graphics processing unit (GPU), a physics processing unit (PPU), a digital signal processor (DSP), a network processor, or some other suitable type of processor.

Memory 906 and persistent storage 908 are examples of storage devices 916. A storage device is any piece of hardware that is capable of storing information, such as, for example, without limitation, at least one of data, program code in functional form, or other suitable information either on a temporary basis, a permanent basis, or both on a temporary basis and a permanent basis. Storage devices 916 may also be referred to as computer-readable storage devices in these illustrative examples. Memory 906, in these examples, can be, for example, a random-access memory or any other suitable volatile or non-volatile storage device. Persistent storage 908 may take various forms, depending on the particular implementation.

For example, persistent storage 908 may contain one or more components or devices. For example, persistent storage 908 can be a hard drive, a solid-state drive (SSD), a flash memory, a rewritable optical disk, a rewritable magnetic tape, or some combination of the above. The media used by persistent storage 908 also can be removable. For example, a removable hard drive can be used for persistent storage 908.

Communications unit 910, in these illustrative examples, provides for communications with other data processing systems or devices. In these illustrative examples, communications unit 910 is a network interface card.

Input/output unit 912 allows for input and output of data with other devices that can be connected to data processing system 900. For example, input/output unit 912 may provide a connection for user input through at least one of a keyboard, a mouse, or some other suitable input device. Further, input/output unit 912 may send output to a printer. Display 914 provides a mechanism to display information to a user.

Instructions for at least one of the operating system, applications, or programs can be located in storage devices 916, which are in communication with processor unit 904 through communications framework 902. The processes of the different embodiments can be performed by processor unit 904 using computer-implemented instructions, which may be located in a memory, such as memory 906.

These instructions are referred to as program code, computer usable program code, or computer-readable program code that can be read and run by a processor in processor unit 904. The program code in the different embodiments can be embodied on different physical or computer-readable storage media, such as memory 906 or persistent storage 908.

Program code 918 is located in a functional form on computer-readable media 920 that is selectively removable and can be loaded onto or transferred to data processing system 900 for processing by processor unit 904. Program code 918 and computer-readable media 920 form computer program product 922 in these illustrative examples. In the illustrative example, computer-readable media 920 is computer-readable storage media 924.

In these illustrative examples, computer-readable storage media 924 is a physical or tangible storage device used to store program code 918 rather than a medium that propagates or transmits program code 918.

Alternatively, program code 918 can be transferred to data processing system 900 using a computer-readable signal media. The computer-readable signal media can be, for example, a propagated data signal containing program code 918. For example, the computer-readable signal media can be at least one of an electromagnetic signal, an optical signal, or any other suitable type of signal. These signals can be transmitted over connections, such as wireless connections, optical fiber cable, coaxial cable, a wire, or any other suitable type of connection.

The different components illustrated for data processing system 900 are not meant to provide architectural limitations to the manner in which different embodiments can be implemented. In some illustrative examples, one or more of the components may be incorporated in or otherwise form a portion of, another component. For example, the 906, or portions thereof, may be incorporated in processor unit 904 in some illustrative examples. The different illustrative embodiments can be implemented in a data processing system including components in addition to or in place of those illustrated for data processing system 900. Other components shown in FIG. 9 can be varied from the illustrative examples shown. The different embodiments can be implemented using any hardware device or system capable of running program code 918.

Thus, illustrative embodiments of the present invention provide a computer-implemented method, a computer system, and a computer program product for estimating a mass of a prepared food product. In one illustrative example, a computer system steers an ultrasonic beam at the prepared food product on a platform. The computer system determines an estimate of the mass of the prepared food product on the platform using response signals detected in response to scanning the prepared food product on the platform with the ultrasonic beam. In another illustrative example, the estimate is a first estimate, and the computer system determines a second estimate of the mass of the prepared food product on the platform using an input mass of raw material used to prepare the prepared food product and an output mass of the prepared food product sold. The first estimate of the mass of the prepared food product and the second estimate of the mass of the prepared food product are combined to form a combined estimate of the mass of the prepared food product. This fusion of the first estimate and the second estimate can provide increased accuracy in determining the mass of the prepared food product.

Thus, one or more illustrative examples overcome a technical problem with estimating a mass of a prepared food product as accurately as desired for use in managing an operation of a food processing facility. For example, issues with weight sensors on platforms, infrared sensors, and camera-based sensors can be reduced using mass estimation system 112 in FIG. 1. This information can be used for determining when and how much raw material is prepared to produce a prepared food product. Further, the information can also be used for other decisions such as purchasing of raw material, staffing, staff schedules, and other suitable actions that can be performed for the food processing facility.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiment. The terminology used herein was chosen to best explain the principles of the embodiment, the practical application or technical improvement over technologies found in the marketplace, or to enable others of ordinary skill in the art to understand the embodiments disclosed here.

What is claimed is:

1. A method for estimating a mass of a prepared food product, the method comprising:
   steering, by a computer system, an ultrasonic beam at the prepared food product on a platform;
   determining, by the computer system, a first estimate of a mass of the prepared food product on the platform using response signals detected in response to scanning the prepared food product on the platform with the ultrasonic beam;
   determining, by the computer system, a second estimate of the mass of the prepared food product on the platform using an input mass of raw material used to prepare the prepared food product and an output mass of the prepared food product sold; and
   combining, by the computer system, the first estimate of the mass of the prepared food product and the second estimate of the mass of the prepared food product to form a combined estimate of the mass of the prepared food product.

2. The method of claim 1 further comprising:
   selecting, by the computer system, a set of regions on the platform with the prepared food product using a Monte Carlo method;
   scanning, by the computer system, a region in the set of regions to scan the prepared food product; and
   detecting, by the computer system, the response signals for the region in the set of regions to form a sample of the mass for the region.

3. The method of claim 2 further comprising:
   repeating the scanning, by the computer system, of the region in the set of regions to scan the prepared food product and the detecting of the response signals for region in the set of regions to form the sample for the region with a different diameter for the ultrasonic beam until the sample of the mass for the region converges by a desired amount.

4. The method of claim 1, wherein the determining, by the computer system, of the first estimate of the mass of the prepared food product on the platform from the response signals detected in response to the ultrasonic beam comprises:

determining, by the computer system, a density of the prepared food product from a variance in a signal strength of the response signals detected in response to scanning the prepared food product on the platform with the ultrasonic beam;

determining, by the computer system, a volume of the prepared food product from a maximum value of the signal strength in the response signals detected in response to scanning the prepared food product on the platform with the ultrasonic beam; and determining, by the computer system, the first estimate of the mass of the prepared food product on the platform using the density and the volume.

5. The method of claim 1, wherein the determining by the computer system, of the second estimate of the mass of the prepared food product on the platform using the input mass of raw material used to prepare the prepared food product and the output mass of the prepared food product sold comprises:

tracking, by the computer system, the input mass of raw material used to prepare the prepared food product and the output mass of the prepared food product sold; and determining, by the computer system, the second estimate of the mass of the prepared food product using an artificial intelligence system with the input mass of raw material used to prepare the prepared food product, the output mass of the prepared food product sold, and a time as inputs into the artificial intelligence system.

6. The method of claim 1, wherein the combining, by the computer system, of the first estimate of the mass of the prepared food product and the second estimate of the mass of the prepared food product to form the combined estimate of the mass of the prepared food product comprises:

assigning, by the computer system, a first weight to the first estimate of the mass of the prepared food product using an artificial intelligence system;

assigning, by the computer system, a second weight to the second estimate of the mass of the prepared food product using the artificial intelligence system; and combining, by the computer system, the first estimate of the mass of the prepared food product that is assigned the first weight and the second estimate of the mass of the prepared food product that is assigned the second weight to form the combined estimate of the mass of the prepared food product.

7. The method of claim 1 further comprising:

emitting the ultrasonic beam from an array of ultrasonic sensors located over the platform.

8. The method of claim 1, wherein the platform is selected from a group comprising a basket, a bin, and a plurality of baskets.

9. The method of claim 1, wherein the prepared food product is selected from at least one of French fries, sausage links, popcorn, green beans, corn salsa, and chicken wings.

10. A mass estimation system comprising:

a computer system that steers an ultrasonic beam at a prepared food product on a platform, determines a first estimate of a mass of the prepared food product on the platform using response signals detected in response to scanning the prepared food product on the platform with the ultrasonic beam, determines a second estimate of the mass of the prepared food product on the platform using an input mass of raw material used to prepare the prepared food product and an output mass of the prepared food product sold, and combines the first estimate of the mass of the prepared food product and the second estimate of the mass of the prepared food product to form a combined estimate of the mass of the prepared food product.

11. The mass estimation system of claim 10, wherein the computer system selects a set of regions on the platform with the prepared food product using a Monte Carlo method; scans a region in the set of regions to scan the prepared food product; and detects the response signals for the region in the set of regions to form a sample of the mass for the region.

12. The mass estimation system of claim 11, wherein the computer system repeats the scanning of the region in the set of regions to scan the prepared food product and the detecting of the response signals for the region in the set of regions to form the sample of the mass for the region with a different diameter for the ultrasonic beam until the sample of the mass for the region converges by a desired amount.

13. The mass estimation system of claim 10, wherein the determining of the first estimate of the mass of the prepared food product on the platform from the response signals detected in response to the ultrasonic beam, the computer system determines a density of the prepared food product from a variance in a signal strength of the response signals detected in response to scanning the prepared food product on the platform with the ultrasonic beam; determines a volume of the prepared food product from a maximum value of the signal strength in the response signals detected in response to scanning the prepared food product on the platform with the ultrasonic beam; and determines the first estimate of the mass of the prepared food product on the platform using the density and the volume.

14. The mass estimation system of claim 10, wherein the determining, by the computer system, of the second estimate of the mass of the prepared food product on the platform using the input mass of raw material used to prepare the prepared food product and the output mass of the prepared food product sold comprises:

tracking, by the computer system, the input mass of raw material used to prepare the prepared food product and the output mass of the prepared food product sold; and determining, by the computer system, the second estimate of the mass of the prepared food product using an artificial intelligence system with the input mass of raw material used to prepare the prepared food product, the output mass of the prepared food product sold, and a time as inputs into the artificial intelligence system.

15. The mass estimation system of claim 10, wherein the combining of the first estimate of the mass of the prepared food product and the second estimate of the mass of the prepared food product to form the combined estimate of the mass of the prepared food product, the computer system assigns a first weight to the first estimate of the mass of the prepared food product using an artificial intelligence system; assigns a second weight to the second estimate of the mass of the prepared food product using the artificial intelligence system; and combines the first estimate of the mass of the prepared food product that is assigned the first weight and the second estimate of the mass of the prepared food product that is assigned the second weight to form the combined estimate of the mass of the prepared food product.

16. A computer program product for estimating a mass of a prepared food product, the computer program product comprising:

a computer-readable storage media;

first program code, stored on the computer-readable storage media, for steering, an ultrasonic beam at the prepared food product on a platform;

second program code, stored on the computer-readable storage media, for determining a first estimate of a mass of the prepared food product on the platform using response signals detected in response to scanning the prepared food product on the platform with the ultrasonic beam;

third program code, stored on the computer-readable storage media, for determining a second estimate of the mass of the prepared food product on the platform using an input mass of raw material used to prepare the prepared food product and an output mass of the prepared food product sold; and fourth program code, stored on the computer-readable storage media, for combining the first estimate of the mass of the prepared food product and the second estimate of the mass of the prepared food product to form a combined estimate of the mass of the prepared food product.

17. The computer program product of claim 16 further comprising:

fifth program code, stored on the computer-readable storage media, for selecting a set of regions on the platform with the prepared food product using a Monte Carlo method;

sixth program code, stored on the computer-readable storage media, for scanning a region in the set of regions to scan the prepared food product;

seventh program code, stored on the computer-readable storage media, for detecting the response signals for the region in the set of regions to form a sample of the mass for the region; and eighth program code, stored on the computer-readable storage media, for running of the third program code and the fourth program code with a different diameter for the ultrasonic beam until the sample of the mass for the region converges by a desired amount.

* * * * *